(12) United States Patent
Hoftman et al.

(10) Patent No.: US 6,354,995 B1
(45) Date of Patent: Mar. 12, 2002

(54) ROTATIONAL LATERAL EXPANDER DEVICE

(76) Inventors: Moshe Hoftman, 22205 Dardenne Ave., Calabasas, CA (US) 91302; Sol Weiss, 7012 Reseda Blvd., #A, Reseda, CA (US) 93063

( * ) Notice: Subject to any disclaimer, the term of this patent is extended or adjusted under 35 U.S.C. 154(b) by 0 days.

(21) Appl. No.: 09/065,767

(22) Filed: Apr. 24, 1998

(Under 37 CFR 1.47)

(51) Int. Cl.[7] .................................................. A61B 1/32
(52) U.S. Cl. ........................................ 600/219; 600/224
(58) Field of Search ................................ 600/224, 222, 600/221, 220, 235, 214, 201, 219; 606/119

(56) References Cited

U.S. PATENT DOCUMENTS

| | | | | |
|---|---|---|---|---|
| 241,036 A | * | 5/1881 | Lyman | |
| 242,443 A | * | 6/1881 | Foote, Sr. | |
| 540,835 A | * | 6/1895 | Gunning | |
| 972,983 A | * | 10/1910 | Arthur | |
| 1,244,751 A | * | 10/1917 | McCleary | |
| 1,428,653 A | * | 9/1922 | Nick | |
| 1,827,497 A | * | 10/1931 | Varney | |
| 2,083,573 A | * | 6/1937 | Morgan | |
| 2,137,121 A | * | 11/1938 | Greenwald | |
| 2,485,939 A | * | 10/1949 | Tedford | |
| 3,517,128 A | * | 6/1970 | Hines | |
| 3,565,061 A | * | 2/1971 | Reynolds | |
| 3,667,474 A | * | 6/1972 | Lapkin et al. | |
| 3,688,773 A | * | 9/1972 | Weiss | |
| 3,759,263 A | * | 9/1973 | Taylor | |
| 4,130,113 A | * | 12/1978 | Garaham | |
| 5,081,983 A | * | 1/1992 | Villalta et al. | 600/224 |
| 5,377,667 A | * | 1/1995 | Patton et al. | |
| 6,096,046 A | * | 8/2000 | Weiss | 600/119 |

OTHER PUBLICATIONS

Cooper Surgical Winter 1996 Catalog, Cooper Surgical Inc., pp. 18, 28.*
Cooper Surgical Spring 1997 Catalog, Cooper Surgical Inc., p. 29.*

* cited by examiner

*Primary Examiner*—Jeffrey A. Smith (57) ABSTRACT

A rotating and lateral expansion device with a relative lateral motion of at least two to four blades. Blades are arranged initially such that their effective forcing planes are substantially axially and facially parallel to each other in a closed position. A lateral motion forcing mechanism is operatively attached to a base plate assembly such that activation of the lateral motion forcing mechanism forces a rotation and sliding action in the base plate assembly which translates into forcing a lateral expansion of a number of the blades. The device permits an examiner to increase the effective diameter of an orifice, such as the vagina, of an examinee.

10 Claims, 13 Drawing Sheets

Figure 15
Top and Bottom Blades
Left and Right Blades

Figure 16
Top and Bottom Blades
Left and Right Blades

Figure 17
Top and Bottom Blades
Left and Right Blades

Figure 18
Left and Right Blades
Top and Bottom Blades

Instrument shaft cross section

ROTATIONAL LATERAL EXPANDER DEVICE

BACKGROUND OF THE INVENTION

The present invention relates to lateral expansion devices with at least two substantially axially parallel blade surfaces that expand from a central axis such that at least an orifice is increased in effective diameter.

It has been known through a very long history of medical expanders and speculums that moving three to five closely aligned parallel blades outwardly can create a valuable orifice expansion effect. Two main classes of these devices emerge from the art. A first class, the more difficult mechanically, maintains the longitudinal axes of the blades in substantially parallel relationship as they outwardly expand against the orifice edges. A second class, with an action typical of the dual bladed vaginal speculum, maintains the base of the blade in a substantially fixed position while the distal ends move equidistant from a central axis. The prior art classes are found in the following U.S. Pat. Nos.: 241,036, 242,443, 540,835, 972,983, 1,244,751, 1,427,653, 1,827,497, 2,083,573, 2,137,121, 2,485,939, 3,517,128, 3,565,061, 3,667,474, 3,688,773, 3,759,263, 4,130,113, and 5,377,667. Vaginal speculums typical of the current state of the art are found in the Cooper Surgical Winter 1996 catalog of CooperSurgical Inc. at page 18 and in the Cooper Surgical Spring 1997catalog of CooperSurgical Inc. at page 29. Two bladed lateral wall retractors typical of the current state of the art are shown in the Cooper Surgical Winter 1996 catalog of CooperSurgical Inc. at page 29.

It is a special object of the present invention to address the function of a combined application of a vaginal speculum and a lateral wall retractor shown Cooper Surgical Winter 1996 catalog of CooperSurgical Inc. at the top illustrations of page 18. In that set of illustrations, it is clear that the combined action of the speculum and retractor present a far more effective view of the cervix. The confused and unstable mass of equipment used to achieve that effect is a disadvantage to the skilled examiner. It is an object of the present invention to at least effect the function of the combined speculum/retractor apparatus of Cooper Surgical Winter 1996 catalog of CooperSurgical Inc. at page 18. It is further an object of the present invention to present an effective new expansion motion for at least two lateral expansion blades whose axes remain substantially parallel during a first expansion motion.

SUMMARY OF THE INVENTION

The present invention comprises a lateral expansion device with a novel relative lateral motion of at least two to four blades. In a four blade embodiment, four blades are arranged initially such that their effective forcing planes are substantially axially and facially parallel to each other in a closed position, although maintaining substantially axially parallel positions throughout a first lateral expansion motion. In that embodiment, two of the blades, a top and bottom blade, are at an initial, closed position axially bracket two other blades, a left and right blade, which are adapted to expand substantially axially directly opposite each other in a straight path to a ultimate positions left and right of their initial positions, respectively.

The lateral motion of the left and right blades is substantially similar to the motion of the blades of the lateral retractor shown and described, as is well known in the art, in the Cooper Surgical Winter 1996 catalog of CooperSurgical Inc. at page 18. Lateral motion forcing means for the present invention includes, as an example, the forcep-type, ratcheting position-locking handles shown and well known to the art for the lateral wall retractor of Cooper Surgical Winter 1996 catalog of CooperSurgical Inc. at page 18.

One form of the four blade embodiment includes four pivotally interlocking base plates, one base plate per blade, adapted such that each blade is secured at one end substantially perpendicular to its own base plate. The following is a description of the motion of the blades from an initial, closed position to a furthermost expanded position. When viewed along an axis from the base plate attachment of the blades outward in the direction of the longitudinal axis of the blades, activation of the lateral motion forcing means forces the forcing plane of the top blade into an angularly smooth sweeping motion upward and to the right with respect to a lateral left hand motion of the forcing plane of the left blade, such that the top blade, in a first portion of the first lateral expansion motion, remains at least partly facially relatively close to and in front of the forcing plane of the left blade. Thus, the left blade moves laterally to the left while the top blade slides upward and to the right, maintaining a relatively continuously increasing force plane comprising the left facing left blade and the upwardly rotating top blade. In a second portion of the first lateral expansion motion, the left blade completes its path to furthest left hand position and the top blade rotates and upwardly moves outward in a relatively longer path as compared to the path of the left blade, such that the preferred final position of the top blade is substantially above and perpendicular the position of the left blade. The motions of the right blade and the bottom blade are opposite to but otherwise identical with those of the left blade and the top blade, respectively, such that in a furthest position away from the initial position, the right and left hand blades are facially substantially parallel and the top and bottom blades are facially substantially parallel.

In summary, the combined action of a left/top blade from the closed position to a furthermost lateral expansion position first develops a continuous combined force plane which lifts an upper portion of an orifice away from the left direction expansion of the left blade and finally results in a orifice opening expanded equally from an original small axis. Such an action, in the four blade embodiment, accomplishes the function of the combined vaginal speculum and lateral wall retractor currently required in the art for complete cervix exposure as shown in the upper illustration of the Cooper Surgical Winter 1996 catalog of CooperSurgical Inc. at page 18.

It should be understood that the blade of the present invention defines a physical piece of material and may comprise one or more rods or solid or perforated plates, such that the force applied to the lateral motion forcing means is translated into a lateral expansion of the blade as at least a part of an imaginary cross sectional forcing plane. The forcing plane is that widest face of an imaginary blade which would still accomplish the objects of the invention. The longitudinal axis of the blade is substantially the lateral cross section center of the blade. Thus, the blades of the present invention may comprise blades which are not facially opposite each other in the closed position, although their lateral expansion motion as part of the forcing planes of the above described motion of the four blade embodiment is substantially the same. In some embodiments, a single rod may be a blade and replace the potentially widest blade face of a forcing plane and still accomplish the relative upward and downward outward rotation of the top and bottom blades respectively with respect to the lateral outward motion of the left and right blades.

Alternate embodiments of the present invention arise from exclusive use of:
1. A top and bottom blade alone.
2. A top and left blade alone.
3. A left, right and top blade alone.

The novel relative motion of a left or right blade with respect to a top or bottom blade is a significant improvement of the present invention. Although many of the most important benefits of the present invention arise from the four blade embodiment, it is clear that at least part of the objects of the present invention will be obtained with use of two or three blades as described above.

The pivotal interlocking base plates with lateral motion forcing means comprise a novel arrangement accomplishment of the lateral expansion action of the present invention. It is preferable the two slotted plates pivotally attach to two solid plates. The solid plates are, on operant sides of those plates respectively, the securing surfaces for the left and right blades and, on the opposite, operator sides of those plates respectively, securing surfaces for the lateral motion forcing means. The slotted plates are, on operant sides of those plates respectively, the securing surfaces for the top and bottom blades. It is a further improvement in the base plates to provide an inside notch-out section into which forceps, probes or the like may rest and/or be secured such that other devices may be used through the generous orifice created by expansion of an orifice by the present invention. It is yet a further improvement in the base plates to provide releasable furthest expansion position means at one end of the slotted plate, such that the slotted plate of the top blade is capable of being released from pivotal attachment to the adjoining solid plate. This action permits location of forceps, probes or similar actuating, viewing or manipulating means between the edge of the orifice created with the present invention and the outside edge of the adjoining solid plate, removing its from the view- and action-blocking effects from the effective orifice created by the present invention.

The further most lateral expansion position of the four blade embodiment places the base plates of the present invention in a framing relationship for a view through the orifice expanded according to the present invention. It is preferable that the base plates will be substantially outwardly curved on an inside edge when viewed from the operator sides, i.e., the view seen by the operator of the device when looking into the expanded orifice comprises substantially a rounded opening framed by the inside edges of the base plates.

It will be understood with the present disclosure that the relative shapes, thickness, compositions and similar variables of the blades comprise a very wide range of effective aspects. Some of the effective shapes and relative configurations are disclosed below. In another embodiment of the top blade, it is shown below that a pivotal attachment may be made to effect the upward motion of the prior art vaginal speculum, such that presentation of the cervix is more effectively made.

It has been found in a prototype that a slight swiveling attachment of the shafts of the lateral motion forcing means with respect to at least one of the solid plates provides excellent expansion initiating action. Without such swiveling attachment, it has been found that initiating expansion according to the present invention is somewhat more difficult than a similar expansion of a lateral wall expander according to the prior art. It is preferred to include such a swiveling attachment between the solid plate and the lateral motion forcing means.

In a further improvement of the present invention, it has been found that a physical blade may comprise a disposable or replaceable portion and a support portion so that a single lateral motion force means and base plate assembly may be used with several blade lengths and/or be replaced between one medical examination or surgical procedure and the next. The support portion is preferably an inverted, substantially U-shaped flattened frame, whereby the tops of the inverted U-shape are secured by welding or equivalent means (as molding in the case of a plastic embodiment of the present invention) to an operant side of the base plate within the cross section area of the appropriate blade force plane. The replaceable blade preferably has a smooth, convex outer face (that face opposing an orifice edge) and two longitudinal lugs on its inner face adapted to initially engage the top of the inverted U-shape and thereby to slide securingly down the legs of the U-shape until forced against the base plate.

BRIEF DESCRIPTION OF THE DRAWINGS

FIGS. 2, 3, 4 and 5 are a perspective view and FIGS. 2A, 3A, 4A, and 5A are a top view of the lateral expansion of a four blade embodiment of the present invention from an initial, closed position to a further most expansion position.

FIG. 2A' is a perspective view and FIG. 2A' is an especially compressed initial, closed position of the present invention.

FIG. 2A" shows a lateral cross section of the blades shown in hidden lines in FIGS. 2B, 4B and 5B.

DETAILED DESCRIPTION OF THE INVENTION

Figure 1:
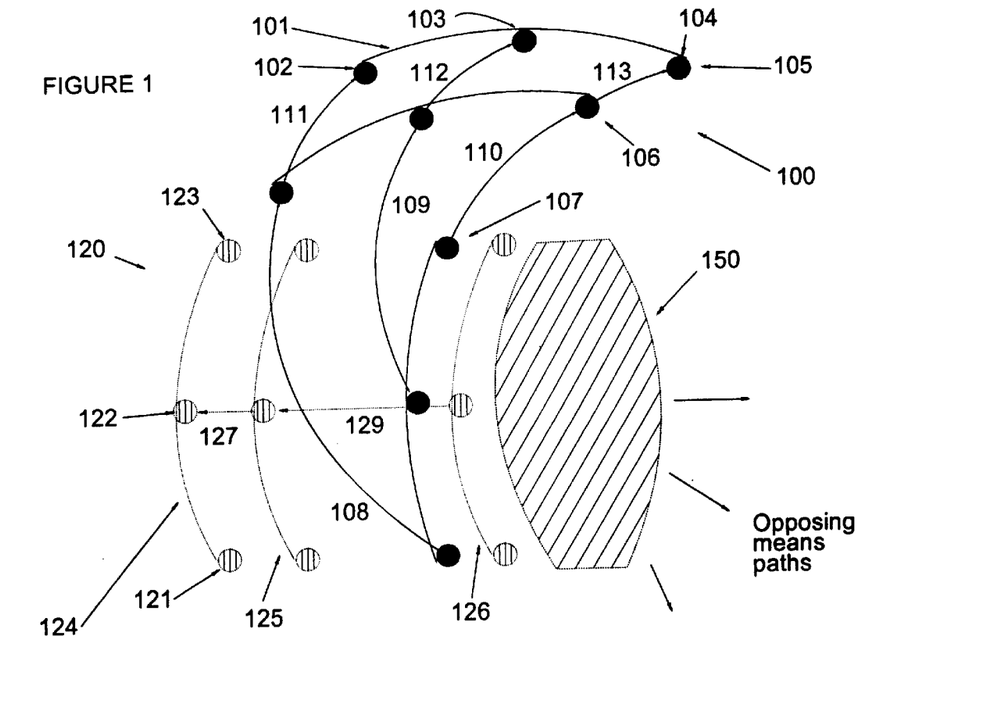
FIG. 1 is a multi-step diagram of left and top blade forcing planes of the present invention from an initial, closed position to a further most expansion position.

FIG. 1 shows a top blade forcing plane 100 and left blade forcing plane 120 in initial, closed positions 107 and 126 respectively. Planes 100 and 120 comprise axes 103 and 122 and ends 101/104 and 121/123 respectively. In traveling from positions 107 and 126 along paths 109 and 129 to intermediate positions 106 and 125, planes 100 and 120 respectively form in the intermediate position a continuous expanded force plane, whereby a left facing force plane is held with an end 123 relatively close to an upward facing force place end 102. The paths 129 is known in the prior art. The relative concurrent relative motion of force planes along paths 109 and 129 to form an expanding continuous force plane combination is novel.

Planes 100 and 120 move into further most expansion positions 105 and 124 along paths 112 and 127 respectively. Positions 105 and 124 align planes 100 and 120 substantially perpendicular with respect to each other. An orifice into which left and top blades are initially inserted in the closed position is thus smoothly and non-traumatically enlarged at least in part by the action of the expansion of planes 100 and 120 against the edges of the orifice (not shown but understood to comprise especially human body orifices or surgical incisions). It will be understood that any fixed or movable axially opposing plate or rod according to the prior art will be sufficient and necessary to be located at some relatively close position to the right of plane 120 at position 126 to obtain the benefits of the present invention with the relative motions of planes 100 and 120 through the closed, intermediate and further most positions. Although it is most preferable that a four blade embodiment be used as shown in FIG. 1A, it is intended that a substantial benefit is still obtainable with the disclosure only of the embodiment shown in FIG. 1.

FIG. 1 shows the paths 108 and 111 of end 102 of plane 100 and the relatively shorter paths 110 and 113 of end 104 of the same plane as it moves from an initial, closed position to an intermediate position to a furthermost expanded position. It is a critical improvement of the present invention over the prior art that the effective blade face presented in plane 100 moves from an initial, closed position upward and to the right to an intermediate position without opening the orifice in an upward distance as much as in the left hand direction while smoothly increasing the effective orifice opening by an ever increasing substantially continuous force plane combining planes 100 and 120. Thus, a substantial object of the present invention is achieved without having to force the blades of the present invention to a furthermost expansion position. For the operator, this means that genetically or procedurally variable orifices in medical procedures, such as vaginal or proctol examinations, may be effectively opened to a widest comfortable or optimally effective position with the device of the present invention without having to force the device fully open. The later disclosed base plates open sufficiently even at an intermediate position to provide a clear and effective view and operating orifice for the operator.

Figure 1A:
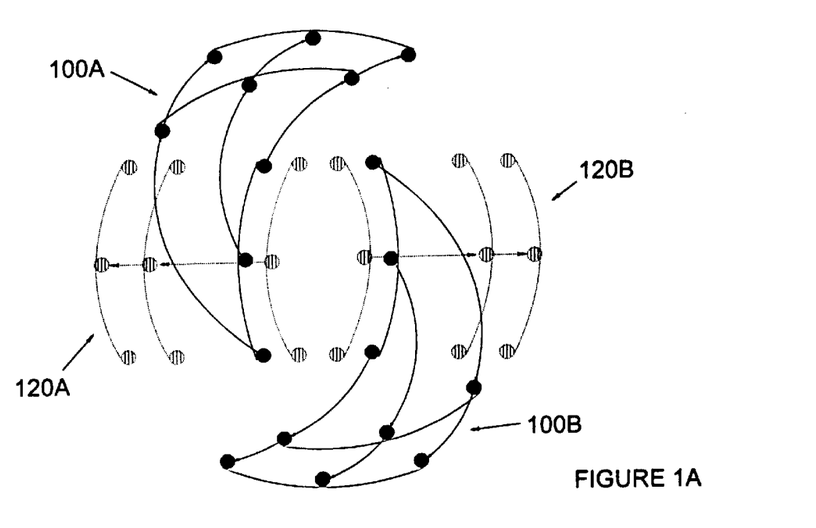
FIG. 1A is a multi-step diagram of left, right, top and bottom blade forcing planes of the present invention from an initial, closed position to a further most expansion position.

FIG. 1A shows left blade 120A opposed to right blade 120B through opposite paths and having the same axes and ends as those shown in FIG. 1. FIG. 1A also shows top blade 100A substantially opposed to bottom blade 100B through opposite paths and having the same axes and ends as those shown in FIG. 1. FIG. 1A shows the relative positions and paths of a four blade embodiment of the present invention. As described above, an intermediate position provides two pairs of broad, curved, combined force planes having moved from a closed position in which insertion of the blades of the force planes is relatively easy.

Figure 2:
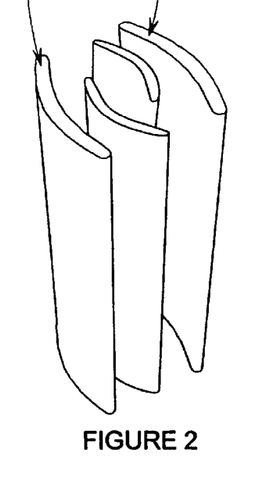
Figure 2A:
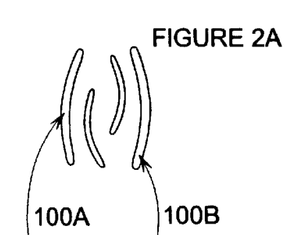
Figure 3:
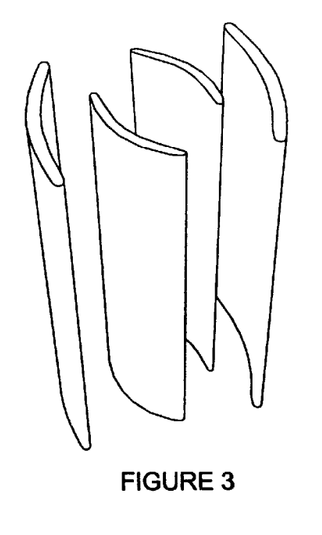
Figure 3A:
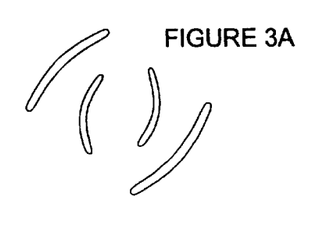
Figures 4, 4A, 5, 5A:
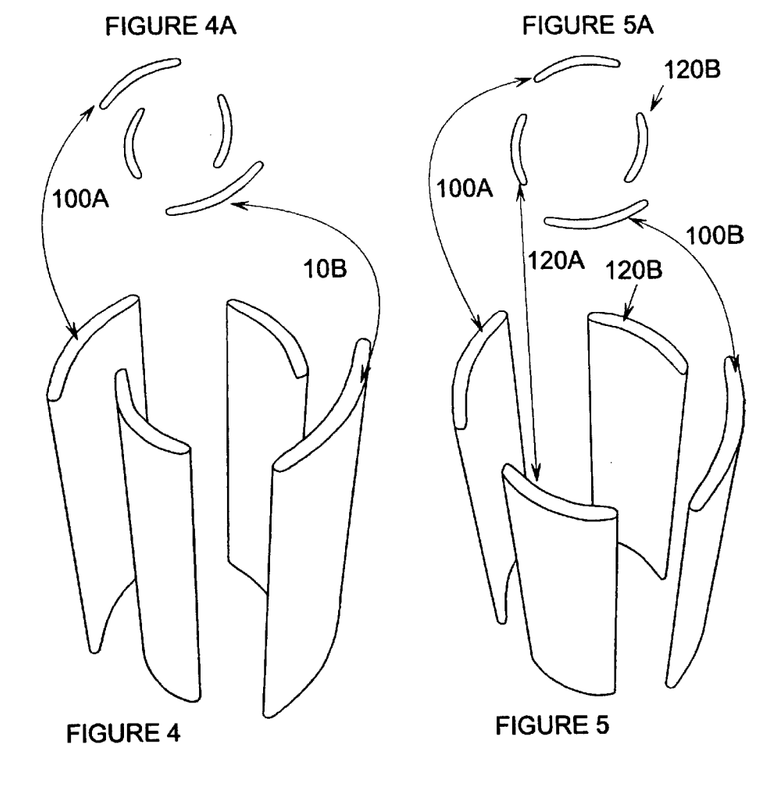
Figure 11:
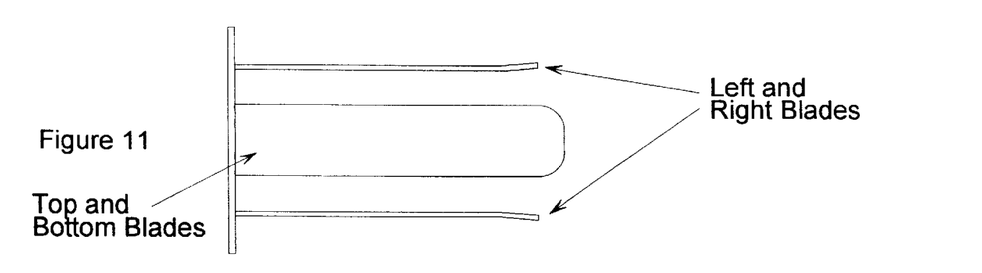
FIGS. 11–18 show relative lengths and shapes of blades of the present invention.
Figure 13:
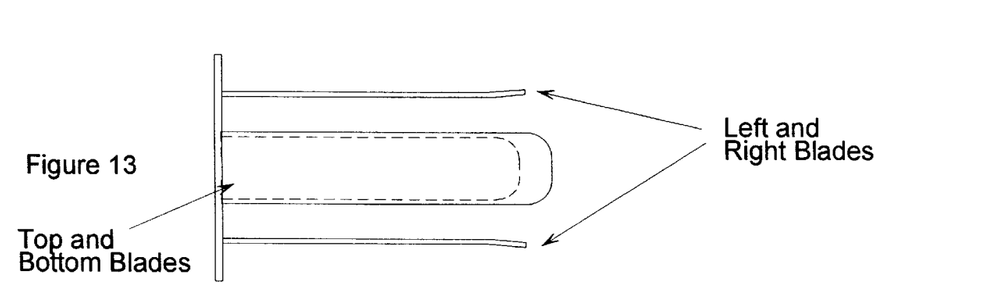
Figure 14:
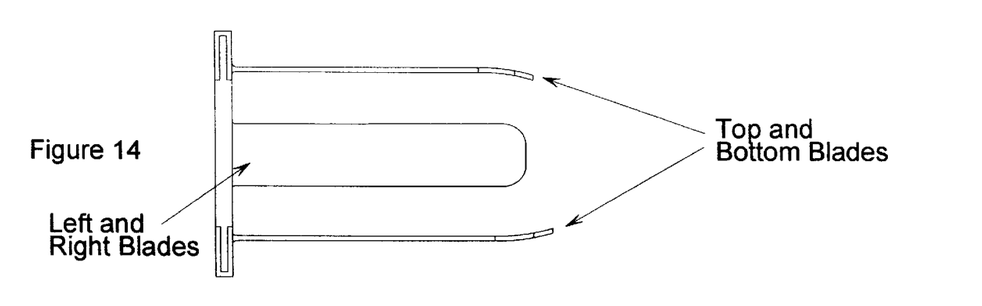
Figure 15:
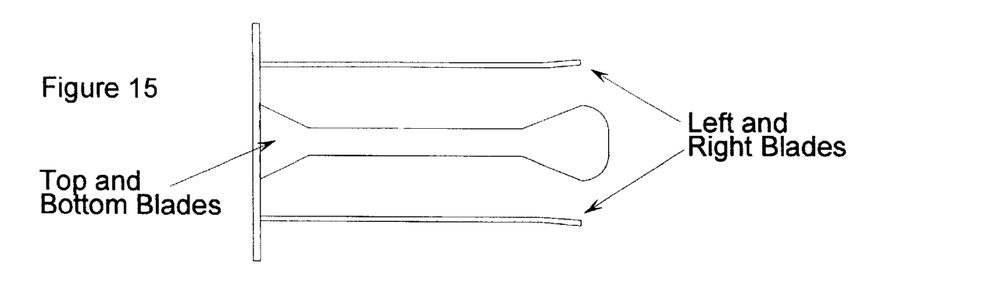
Figure 16:
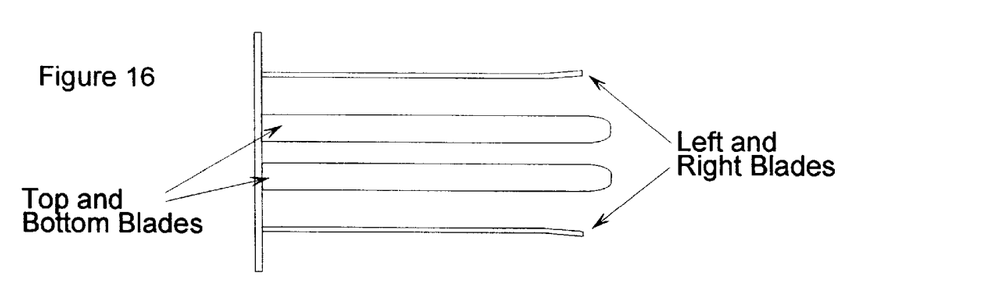
Figure 17:
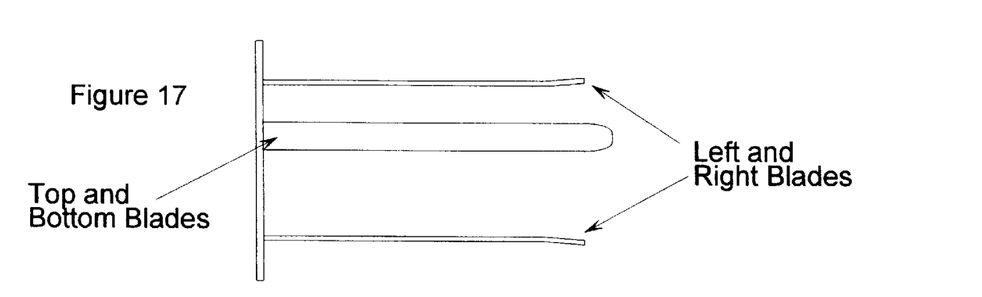
Figure 18:
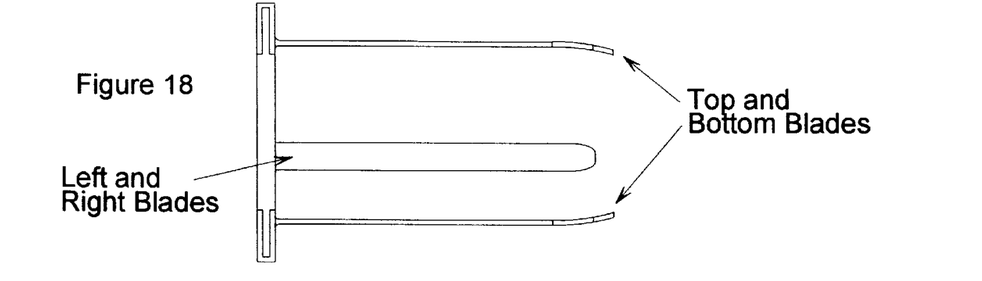

FIGS. 2/2A, 3/4A and 5/5A correspond to an initial, closed position, and intermediate position and a furthermost expanded position of an embodiment of the blades of the present invention. FIGS. 3/3A shows a blade position between that of FIGS. 2A and 4A. The left and right blades shown in these figures are not as cross sectionally wide as the potential force plane for those blades, however, it can be seen in FIG. 2A the vertical offset arrangement permits a smaller overall cross section area for all the blades into an orifice while still obtaining substantially all the benefits of the present invention. FIGS. 2'/2A' show in perspective and cross section just how tightly this embodiment can be pressed together along their longitudinal axes to achieve an extremely small overall cross section for all the blades to ease insertion into an orifice. A most preferred set of blades for vaginal and proctol examinations are those shown in FIGS. 2–5 with relative lengths and ends for the blades shown in FIGS. 13 and 14. The left and right blades curve gently outward at their ends to prevent slipping of the device from the orifice, and the top blade is slightly longer than the left and right blades while the bottom blade is slightly longer than the top blade. The top and bottom blades curve gently inward at their ends, such that in the closed position the bottom blade presents a single curved insertion edge in advance of and slightly sheltering the top blade leading edge, whereby the combined effect of the inward slope of the top and bottom blades completely shelters the left and right blades during insertion, making initial insertion resistant only to about the width and cross section area of the bottom blade alone. A variation of FIGS. 13 and 14 are shown in FIGS. 11 and 12, whereby the top and bottom blades are about the same length.

FIGS. 15–18 show further variations of blade lengths and shapes. It will be clear from this disclosure that the furthest cross section boundaries of force planes in which physical blades are located may contain a wide variation of shapes, number of separate blades and any variation of blade lengths to accomplish an almost endless objects of orifice expansion, whether or not within the medical field.

Figure 12:
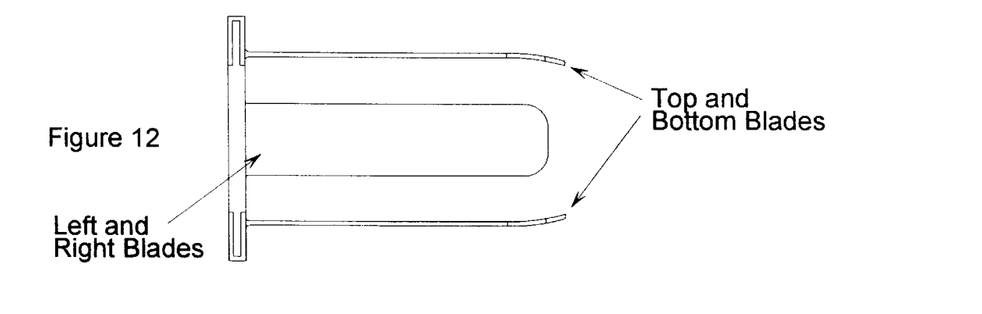
Figure 19:
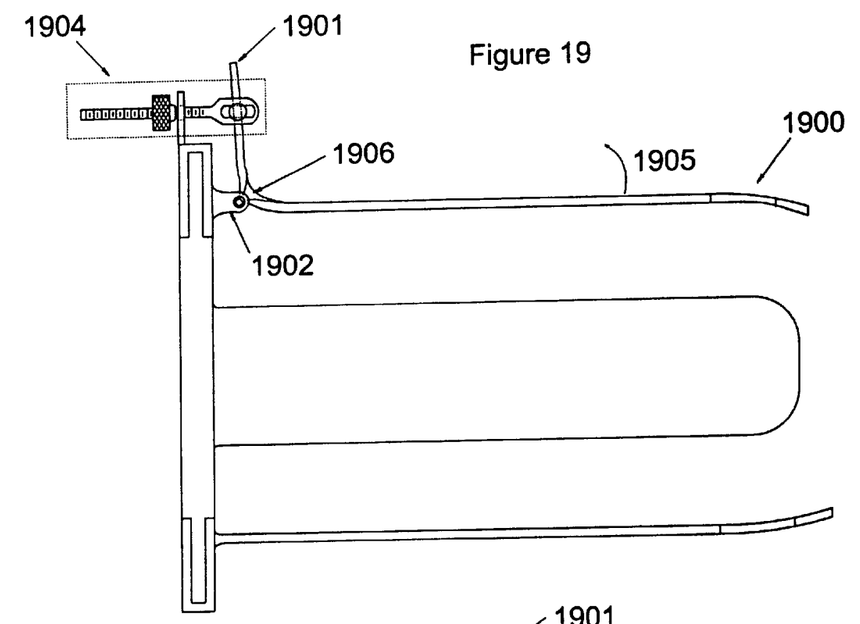
FIGS. 19 and 20 show an upwardly pivotal top blade to accomplish the cervix exposing function of the vaginal speculum of the prior art.
Figure 20:
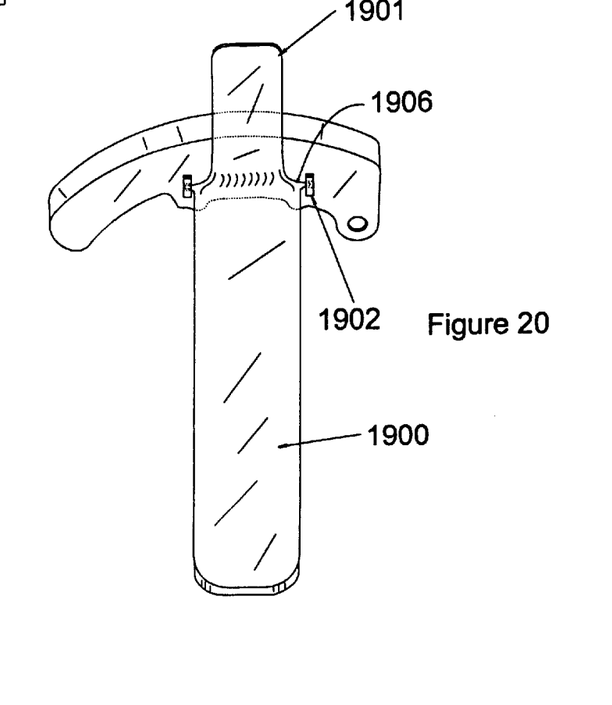

FIG. 19 is substantially the same as FIG. 12 with respect to blade lengths, widths and face shapes. FIGS. 19 and 20 are shown with adaptations sufficient to accomplish the cervix exposing function of the upper spatulate part of a vaginal speculum. With the prior art vaginal speculum, the upper spatulate part is inserted into the vagina rotated downward into contact with the lower spatulate part. After insertion, the upper spatulate part is rotated upward to cause the cervix to "present" into the view of the examiner. FIGS. 19 and 20 show a top blade adapted to rotate upwards after insertion and expansion to the furthermost expansion position. The upward rotation of top blade 1900 through path 1905 is effected by finger or thumb pressure on lever part 1901, which is integral with top blade 1900. Position securing means 1904 in FIG. 19 comprises a prior art assembly of threaded shaft and a knurled position nut adapted such that the position of the nut fixes the upward position of top blade 1900 in path 1905. Rotation extensions 1906 of top blade 1900 extend into lugs 1902 which extend from the operant surface of the top blade base plate and are adapted to rotatingly receive extensions 1906.

Figures 2B, 4B:
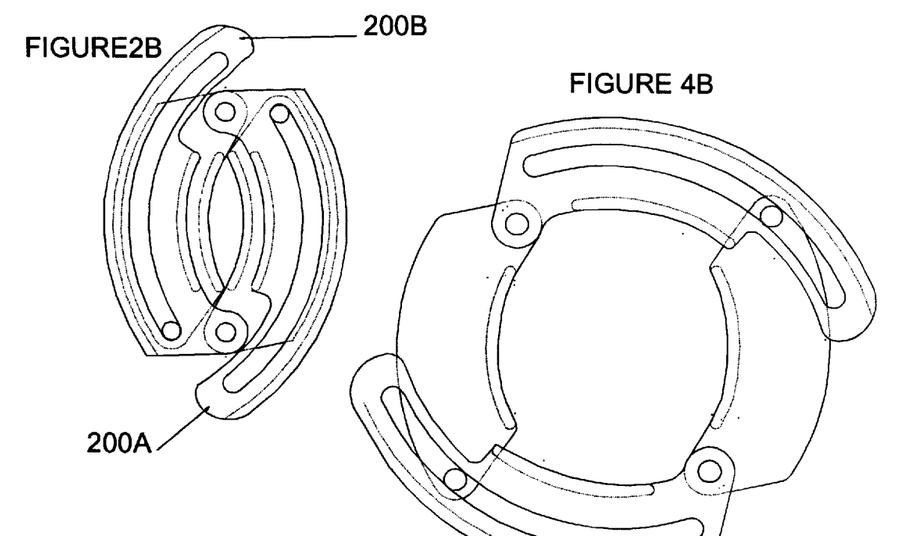
FIGS. 2B, 4B and 5B are positions of the solid and slotted base plates of the present invention substantially corresponding to the positions of the blades in FIGS. 2A, 4A and 5A.
Figure 5B:
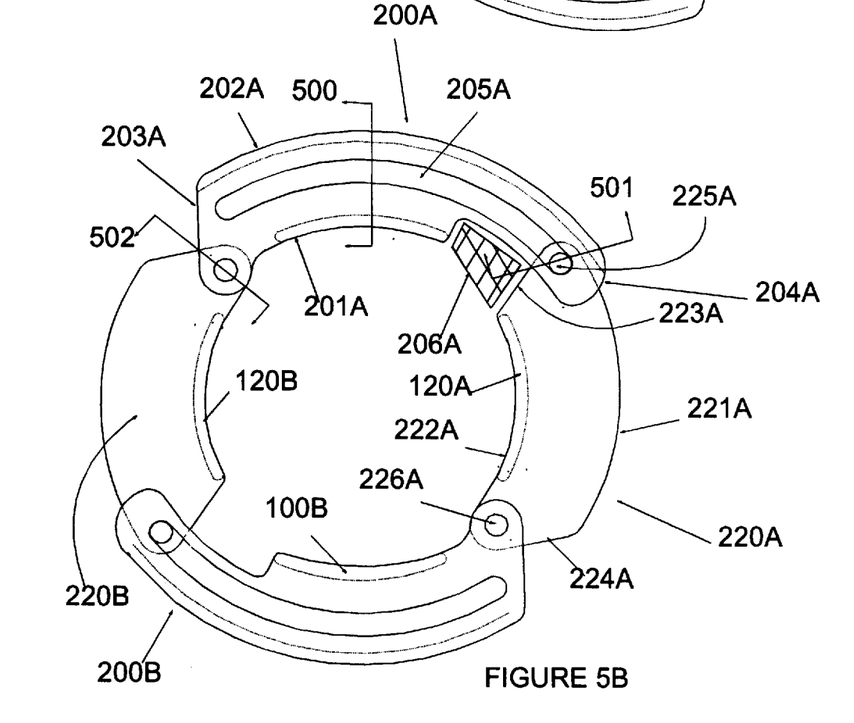
Figure 5C:
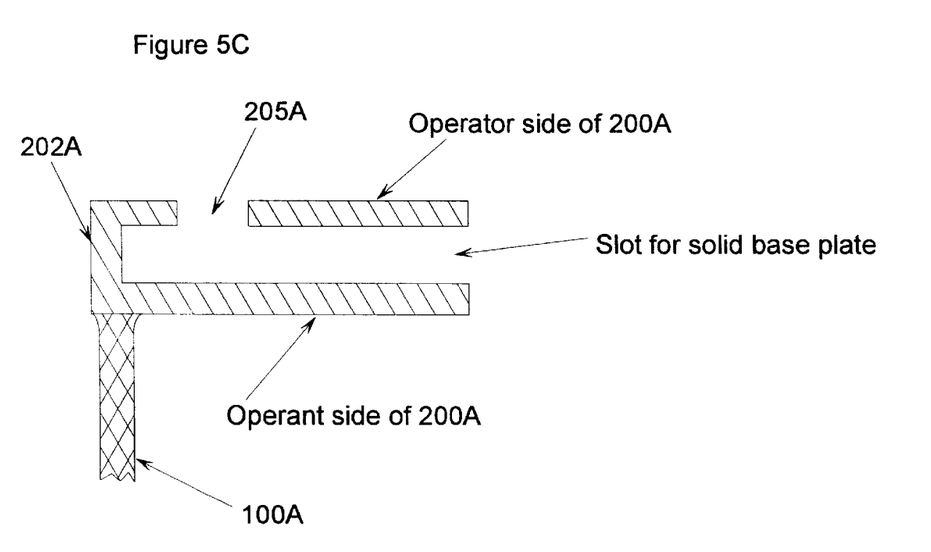
FIGS. 5C, 5D and 5E are cross sections 500, 501 and 502 respectively in FIG. 5B.
Figure 5D:
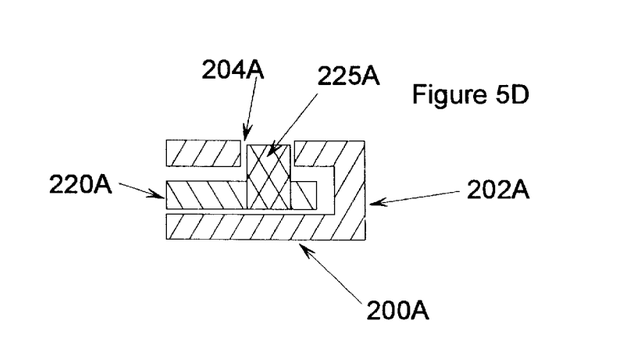
Figure 5E:
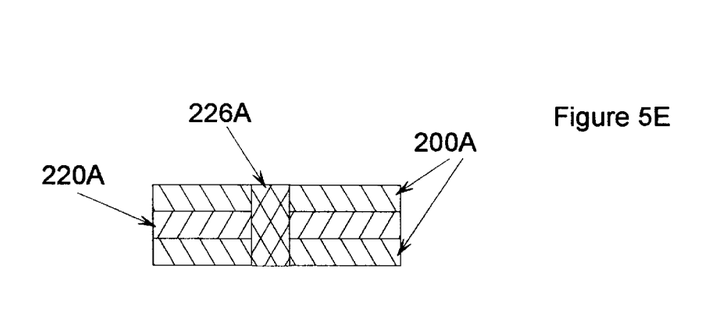

Preliminary to discussion of the base plates and their operation, FIG. 2" shows the general cross section arrangement in a closed position of the blades shown in broken, hidden lines in FIGS. 2B, 4B and 5B, which correspond to the closed, intermediate and furthermost expansion positions described above. Blades 100A/B and 120A/B in FIGS. 2B, 4B and 5B are preferably welded to the operant side (the side opposite of that shown in plan view in FIGS. 2B, 4B and 5B) of the base plates 200A/B and 220A/B respectively. As such, the blades are substantially perpendicular to the operant surface of the base plates. Although it is clear that some functions may be added to the matched base plates, the present invention has achieved a substantial reduction in manufacturing complexity in the base plate assembly to transmit the force of the lateral motion forcing means to the blades by requiring only two types of base plate pieces. Base plates 200A and 200B are preferably identical, as are base plates 220A and 220B. Base plates 220A and 220B are the solid base plates described above and preferably comprise a solid metal piece with an inside curved edge 222A and an outside curved edge 221A. Pin 225A is mounted flush with the operant side of base plate 220A and extends slightly above of its operator side in a fixed position at about the intersection of edge 221A and inward slanted edge 223A. The slanting of edge 223A is critical to easy closing to the closed position of the base plates. A second pin 226A passes rotatably through base plate 220A and extends through and is flush with the operant and operator sides of base plate 200A, such that securing means are effected to maintain the pin in place and allow base plates 200A and 220A rotate in a plane with respect to each other. FIG. 5E shows a cross section 502 of the area about pin 226A, showing the relationship just described.

Base plate 200A comprises an inner curved edge 201A and an outer curved edge 202A, with an outward slanted edge 203A and a curved end edge 204A. The operant and operator sides of base plate 220A are separated metal plates supported by a solid wall along edge 202A, such that all the other edges present an open slot for free movement of the solid base plate therethrough. Such relative positioning is shown in FIG. 5D for section 501 through pin 225A. Slot 205A runs approximately midway between edges 201A and 202A between ends 203A and 204A to accommodate rotational expansion of base plate 200A with respect to the solid base plates. Section 500 in FIG. 5C shows this structure in cross section view. The relationship of the other matched base plates and pins not specifically named in this description will be appreciated with respect to the above description.

It will be appreciated that the solid base plates 220A/B (and therefore the outer faces of the blades potentially filling the force planes perpendicular to the operant sides of those base plates) have substantially no orifice-affecting rotation during the motion from closed to furthermost expansion positions. Those base plates just move laterally outward with their attached blades.

To further describe the action of the top and bottom blades, reference is now made to a central orifice axis of an orifice to be expanded, into which the blades of the present invention are inserted, and with further reference to the outward face paths of the blades of solid base plates 220A/B. Base plates 200A and 200B move slidingly and rotationally about pin 226A (or its counterpart on the other slotted base plate) to continuously move the outer faces of the blades potentially filling the force planes perpendicular to the operant sides of those base plates laterally outward and toward a furthermost expanded position defining planes effectively perpendicular to the force planes of the left and right blades. Until an intermediate position is passed by the top and bottom blades wherein, for example, an edge at end 102 of FIG. 1 moves upward and effectively separated from edge 123, the left and top blades provide an ever increasing combined force plane face laterally and rotationally away from the central orifice axis. It is apparent to the skilled person with this disclosure that, as shown in FIG. 1, some opposition means 150 must be fixed or laterally and/or rotationally in motion generally opposite to the expansion paths of force planes 100 and/or 120 to effect an orifice opening effect in conjunction with force planes 100 and 120. It will be clear that opposition means for a four blade embodiment comprises a substantially mirror image motion of another pair of force planes as in FIG. 1A. Some other fixed blade or post is an effective alternative for opposition means 150.

Figures 23, 24, 25, 26:
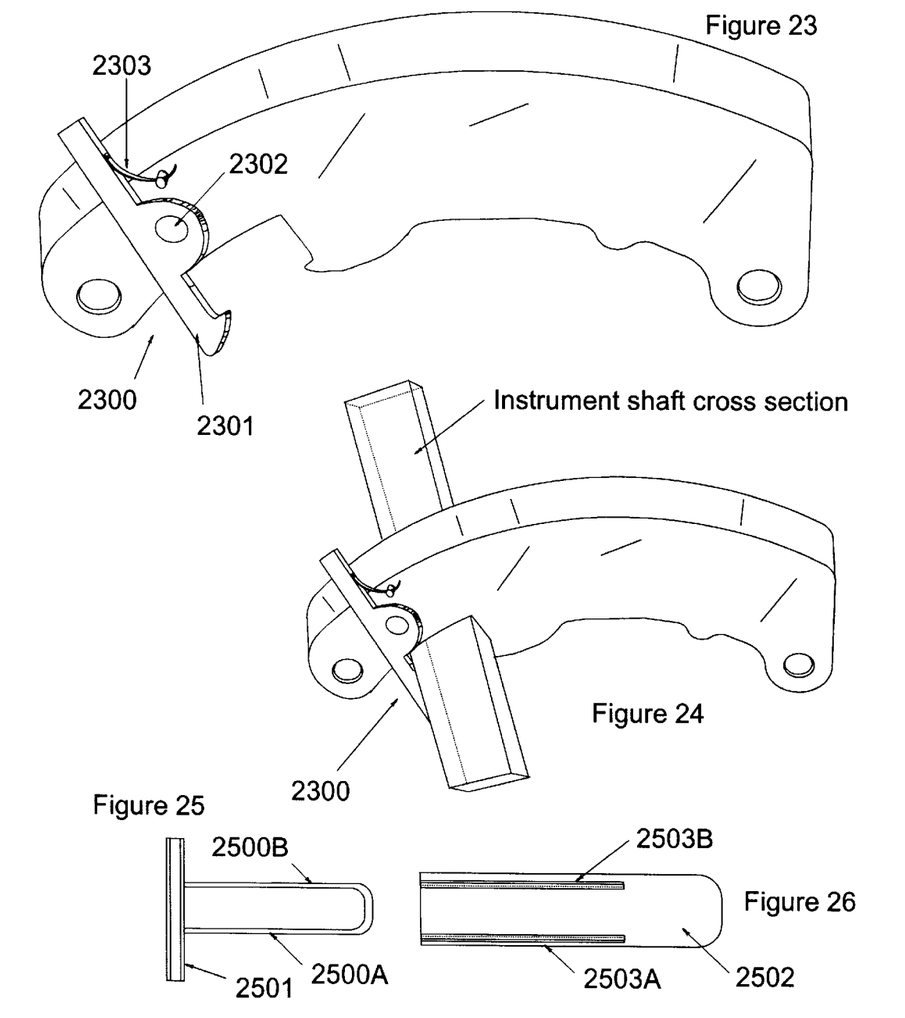
FIGS. 23–24 show separate and assembled views of the removable blade embodiment of the present invention.
FIGS. 25–28 show views of means for disposable or replaceable blades for the combination lateral force means and the base plate assembly.

In addition to the advantages of the present invention, edge 201A for slotted base plates is preferable provided with a substantially rectangular notch out area 206A so that instruments used by an operator reaching from the operator side into a cavity opened and/or created by the lateral expansion may be moved out of the line of sight into the cavity by having them rest in cross section within notch out area 206A. In a further embodiment, FIGS. 23 and 24 show latching means 2300 providing for securing of the reaching instruments onto the slotted base plates. Latch piece 2301 is fixed to the operator or operant side of a slotted base plate by pin 2302 and held in place by spring means 2303. FIG. 24 shows the effective securing of an instrument cross section onto the slotted base plate by means of opposing latching means 2300 to an extension of the inner edge of the slotted base plate.

Figures 6, 7:
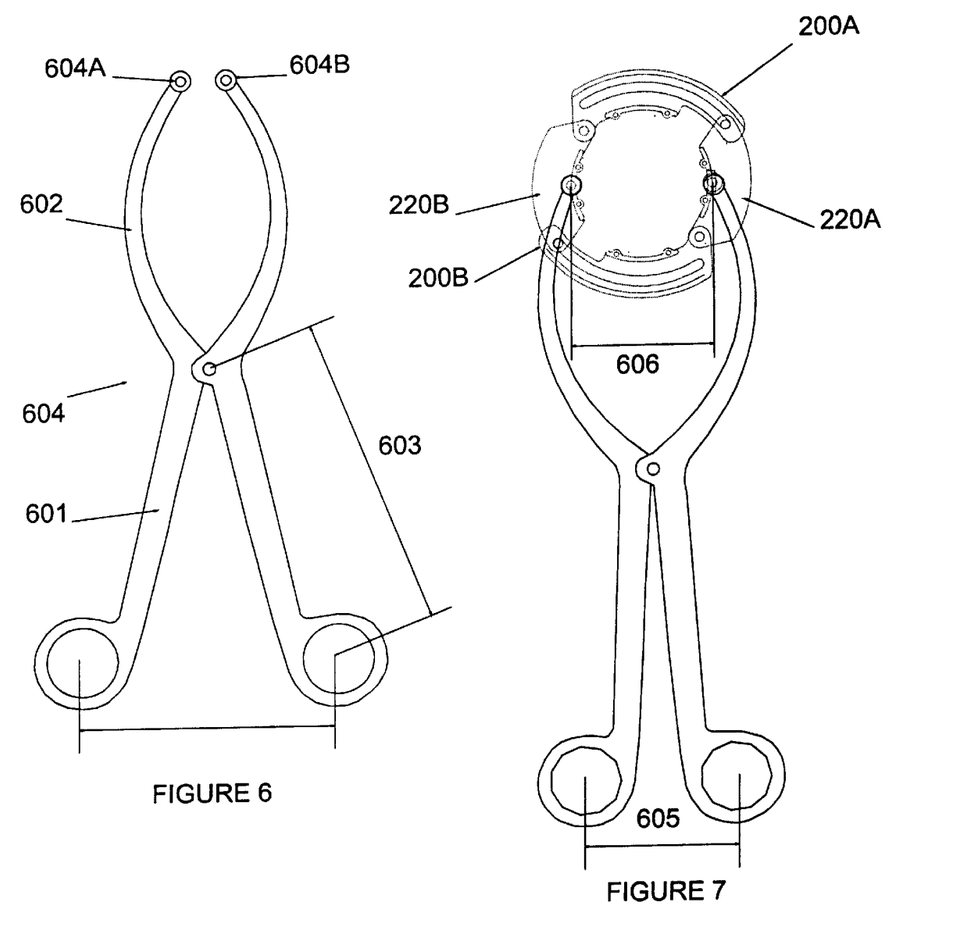
FIGS. 6 and 7 show lateral motion forcing means in an initial, closed and further most expanded position, with the base plate configuration of FIG. 5B shown in broken lines in FIG. 7.
Figure 8:
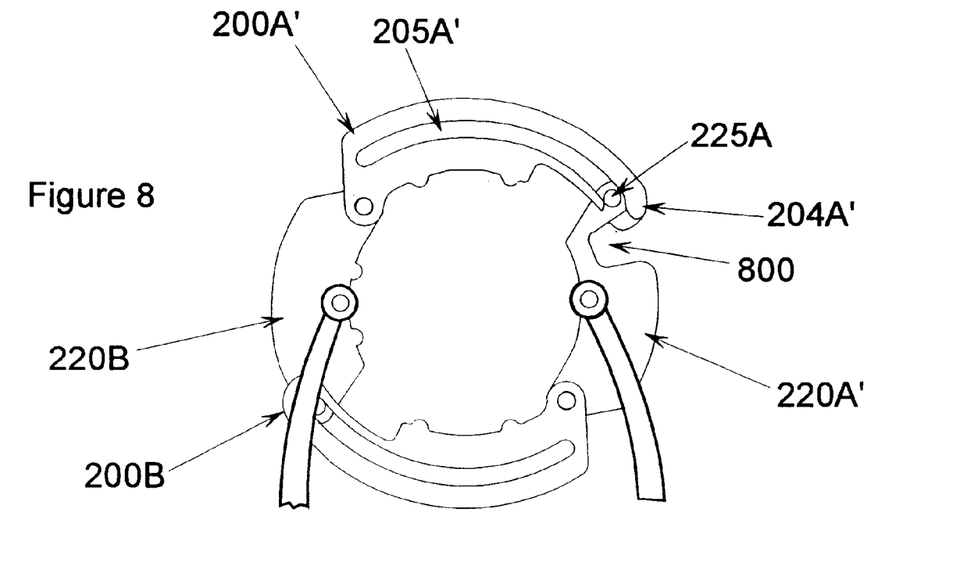
FIGS. 8 and 9 show the releasable slotted plate embodiment, whereby in FIG. 9 is shown the upward release of the slotted plate from the solid plate.

An example of attachment of forcep like lateral motion forcing means 600 is shown in FIGS. 6 and 7. Handle section 601 with a length 603 and attachment section 602 are separated at the hinge pin location therebetween. Attachment means 604A is intended for pinned or welded attachment to the operator side of base plate 220B as shown in FIG. 7. Attachment means 604B is intended for pinned or welded attachment to the operator side of base plate 220A as shown in FIG. 7. Attachment means 604A/B are preferably located close to the inside edge of the base plates to which it attaches. FIG. 7 provides an operator's view of the cavity created or opened thereto by the expanded orifice according to the device and method of the present invention with a view width 606 defined by the inside edges of the base plates. Width 604 is contracted to width 605 by thumb and finger motion to effect a forced lateral expansion motion of the blades attached to the base plates shown in broken lines in FIG. 7.

Figures 21, 22:
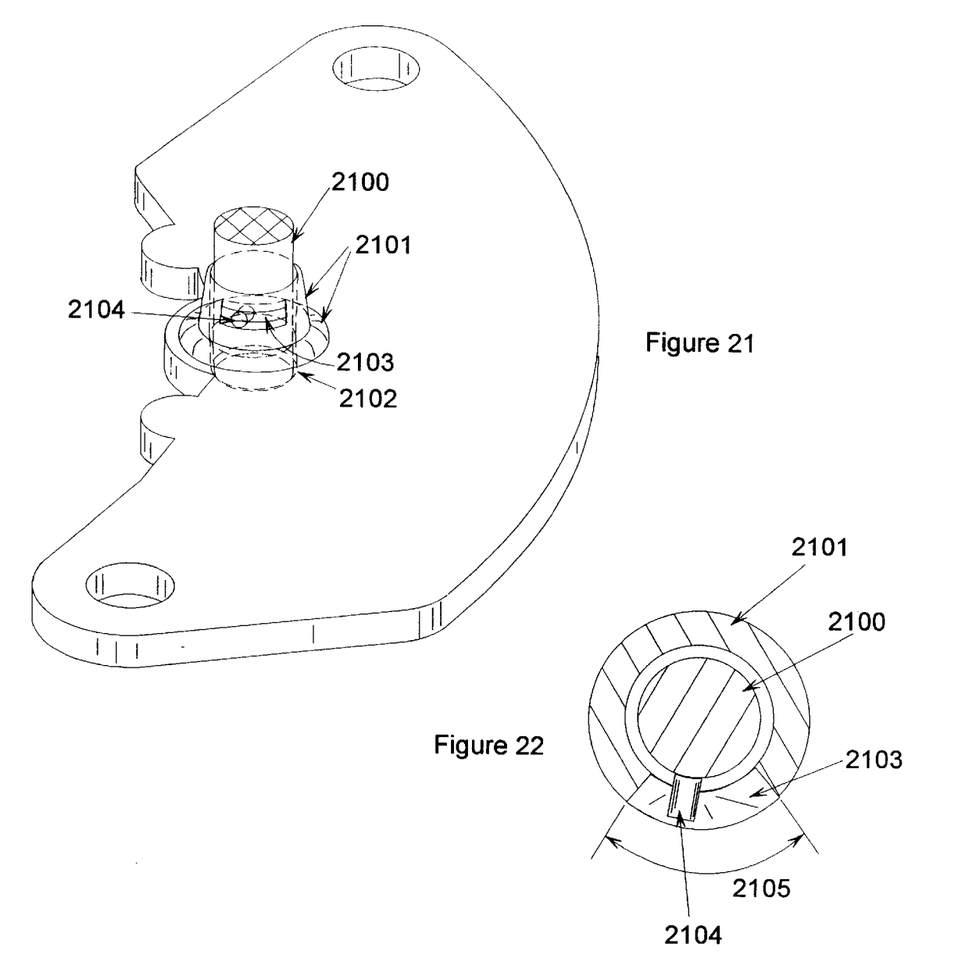
FIGS. 21 and 22 show a perspective view of the swiveling attachment of the lateral motion forcing means to the solid plate.

FIGS. 21 and 22 show a detail perspective and cross section adaptation of the attachment means 604A or 604B to provide slight swiveling attachment of the a shaft 2100 fixed to the free end of the attachment section (not shown) and rotatingly fixed to a solid base plate. Collar means 2101 are welded or similarly attached to the operator surface of the solid base plate. Shaft 2100 is freely rotatable within the bore of the collar means and the adjacent hole 2102 through the solid base plate. Rotation restriction means are provided with slot 2103 and pin 2104. As seen in cross section of shaft 2100 at the level of slot 2104 in FIG. 22, pin 2104 is fixed to shaft 2100 and restricts rotation of shaft 2100 to a restricted path 2105. This swiveling attachment is preferred to provide mechanical looseness to the entire base plate assembly which is thereby improves sliding and rotational freedom without excessive hand pressure on the lateral motion forcing means.

Figure 9:
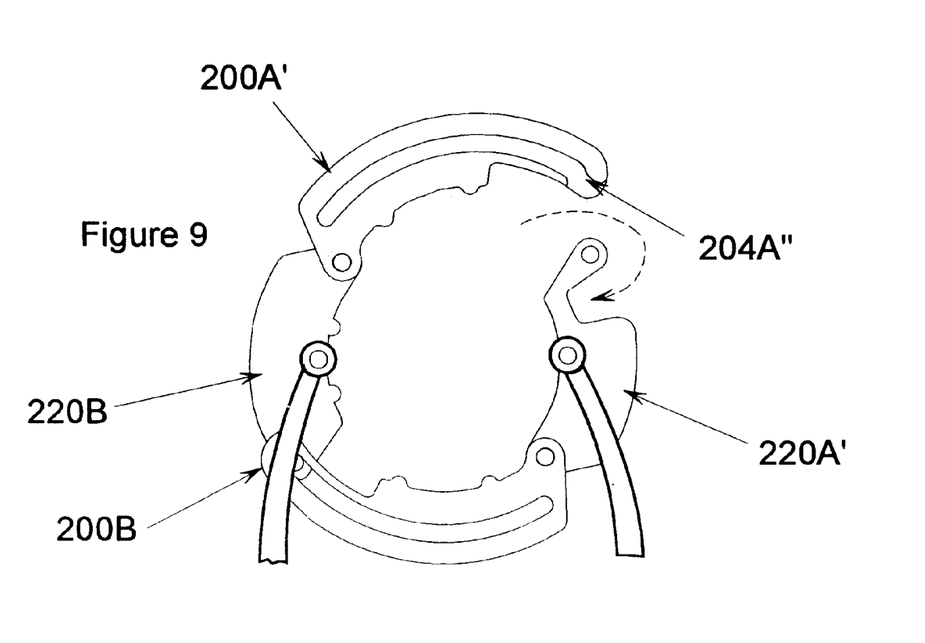

In yet a further improvement of the present invention, FIGS. 9 and 10 show an adaptation of the top blade base plate 200A', such that an opening 204A" is made in end plate 204A' only to the operator side plate extending the slot 205A' to eliminate restraint of the travel of pin 225A within the slot 205A' at that end of the slot. Thus, end 204A' of base plate 220A' is rotatable around pin 226A upward away from the base plate 220A'. When this motion is accomplished with the device expanded into an orifice, the extension shaft of a device used to reach into the orifice may be moved outside of the inside viewing area defined by the inside edges of the base plates and into notch out area 800 in base plate 220A'. The opposed force of the edge of the orifice will tend to hold the device securely in place against the outer face of the blade of the solid plate. The upward rotation of base plate 200A' is then reversed and pin 225A is returned to slot 205A' so that the base plate assembly in stable and secure.

Figure 27:
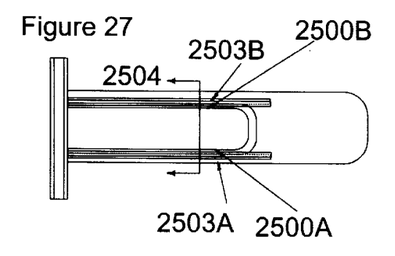
Figure 28:
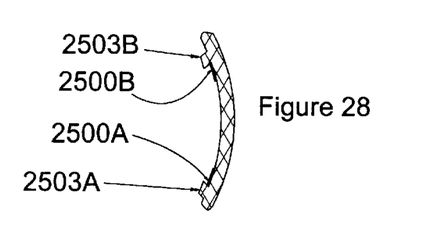

As described above in the Summary of the Invention, another embodiment of the present invention comprises means for disposable or replaceable blades for the combination lateral force means and the base plate assembly. As shown in FIG. 25, a U-shaped frame with legs 2500A/B is secured substantially perpendicular to the operant face of base plate 2501. The U-shaped frame is the most preferable of several possible support means for a disposable or replaceable blade, among the others being rods and the like. FIG. 26 shows a plan view of the curved inner face of removable blade 2502 whose outlines generally define the outer edge of the force plane typical for the size of base plate 2501. Longitudinal lugs 2503A/B are parallel to the longitudinal axis of blade 2502 and are adapted to lean toward the longitudinal axis of blade 2502 at an acute angle so to quickly and easily securingly engage legs 2500A/B respectively, as shown in FIG. 27. FIG. 28 is a cross section 2504 of FIG. 27 and shows the arrangement just described. There are several advantages of the removable blade embodiment. Different blade lengths and widths may be used with the same lateral motion forcing means and base plate assembly, reducing the cost for having the three standard sizes of vaginal speculum available as separate instruments. It is well known in the art that a small (typically pediatric), medium and large (and sometimes long) sizes of vaginal speculums and lateral wall retractors are available for vaginal examinations depending on the size and weight of the examinee. It will be clear to the skilled person with the present disclosure that the blade lengths of the present invention in its several embodiments may be adapted to approximately those of the small (typically pediatric), medium and large (and sometimes long) sizes of vaginal speculums to achieve the superior results of the present invention over the prior art two blade speculum and the lateral wall retractor combination.

It is another embodiment of the present invention to provide on the inside surface of a blade the type of tube/conduit holder as are well known in the art of vaginal speculums, which tube/conduit holders comprise generally two arcuate, opposed metal or polymer extensions of the inside surface of the upper spatulate blade and are adapted to hold in place evacuation conduits for fluids or surgical procedure generated vapor or smoke. Such tube/conduit holders are known in the art to comprise means for securing in place externally powered or chemically induced lighting means for examination of vaginal walls. It will be appreciated that the instrument holding means described above comprise one way to hold in place such tubes/conduits, although the embodiment of this paragraph intends that the prior art tube/conduit holder be adapted to attach or extend from the inside surface of one of the blades of the expander of the present invention. The skilled person will appreciate that such a prior art tube/conduit holder has a substantial elevation above the surface to which is it secured, i.e., the inside surface of the vaginal speculum. In the prior art vaginal speculum with a prior art tube/conduit holder, insertable position closure of the separate spatulate blades of the speculum is achieved with installation of the prior art tube/conduit holder within the outwardly flared, handle attachment end of the spatulate blades. The blades of the present invention do not obtain such a flared section. To accommodate the installation of the prior art tube/conduit holder on the inside surface of a blade 100A or 100B, the blade may be adapted with a longitudinal indentation from the inside surface toward the outside surface sufficiently deep to permit complete intial position closure (close association for insertion) of the blades while raising the cross sectional area through the indentation section only slightly. The longitudinal length of the indentation section is preferably moved as close to the blade attachment point as possible to preserve the very small cross sectional area of the blade presentation at their ends for ease of insertion. It is preferable that the longitudinal length of the indentation section be at least about 1–2 inches in length and comprise a cavity on the inside surface of about the thickness of the tube/conduit to be secured therein.

Figure 29:
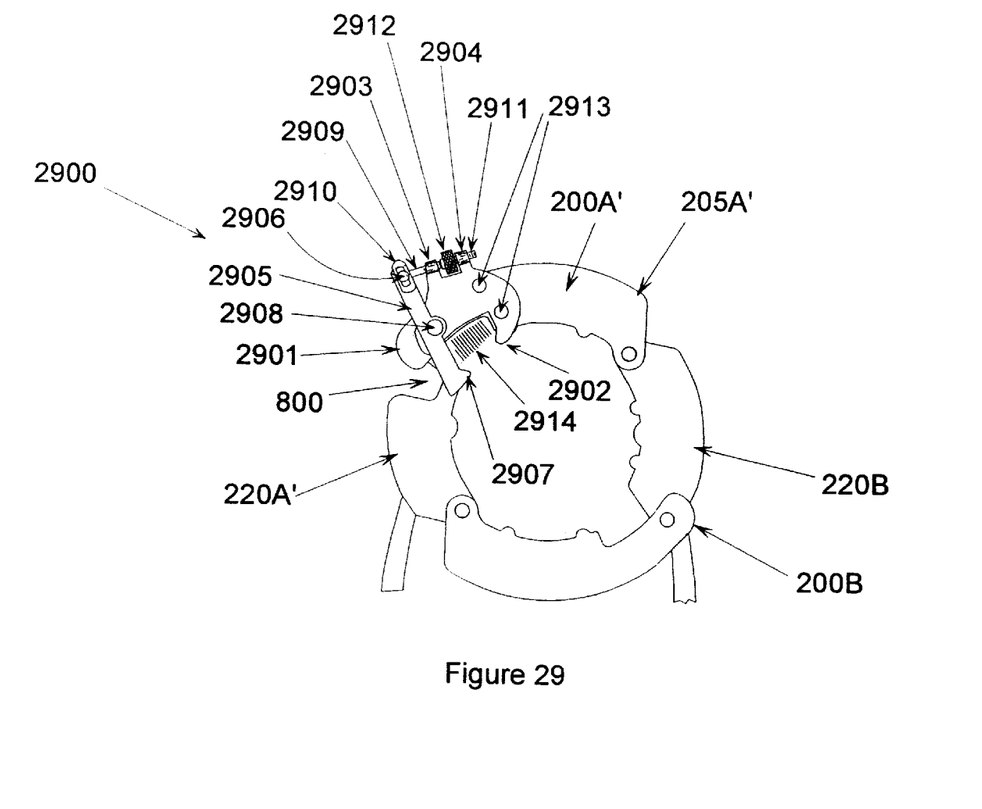
FIG. 29 shows a view of an embodiment of the present invention provided with a tube/conduit holder.

Another embodiment of the present invention is now discussed with reference to FIG. 29. As well similarly described and shown in FIGS. 23 and 24, the present invention is adaptable for installation of an instrument/tube holder that may support away from the field of view down the longitudinal length of the blades shafts of instruments and/or tubes for fluid flooding or evacuation. The instrument/tube holder 2900 of FIG. 29 comprises the substantially flat plate 2901 attached to blade holding side of piece 200A' with pins 2913, whereby the plate 2901 is extended in an upper portion upwardly with two relatively narrow finger-like projections. Those projections are then bent and curled in the direction of the viewer observing FIG. 29 and bent over still further until a tip of the projection approaches the surface of plate 2901 to form two shaft retaining projections 2903 and 2904 adapted to accommodate a loose but retaining fit for threaded shaft 2911. Shaft 2911 extends through the preferably cylindrical internal voids of projections 2903 and 2904 to slotted end 2910, which is a small flattened plate with a slot in it, the slot being adapted to have slideable within it the shaft portion of a headed pin extension 2906 extending from an extended portion of handle 2905. This headed pin extension/slotted end combination is well known in the art of two bladed vaginal speculums as means for securing a threaded shaft adjustment device between the headed pin extension on the upper blade thumb handle and the yoke, although the present embodiment comprises securing means on either side of a knurled nut 2912, which is rotatable about threaded shaft 2906. The effect of providing this embodiment's improvements over the embodiment of FIGS. 23 and 24 is that a single finger rotation of nut 2912 will cause threaded shaft 2911 to be forced along a common axis of the internal voids of projections 2903 and 2904 and therefore results in handle 2905 rotating about pin 2908, forcing to a new and fixed position the projection 2907 either toward or away from an instrument shaft or tube to be retained in zone 2914, whereby the instrument shaft or tube are also retained with extension 2902 of plate 2901. The length of shaft piece 2909 may be adjusted to provide for securing small or large diameter instrument shafts or tubes, as well as the degree of projection of projections 2902 and 2907 into zone 2914.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

What is claimed is:

1. A rotating and lateral expansion device adapted to reach, with relation to a central orifice axis of an orifice, left and top furthermost expansion positions from an initial closed position and passing through an intermediate position comprising:

(a) at least two blades and an opposing blade means, each having an effective longitudinal axis substantially parallel to that of the other longitudinal axes, each adapted to have its longitudinal axis remain substantially parallel to the others throughout lateral expansion of the blades from the central orifice axis during an orifice expansion and each having an outer face adapted to forcingly engage an orifice edge and at least laterally expand the orifice edge from the central orifice axis during an orifice expansion;

(b) the first blade comprising a top blade and the second blade comprising a left blade, whereby the top and left blades lie within top and left blade force planes, respectively, and the outer faces of the left and top blades correspond to at least part of an outer face of the left and top blade force planes, respectively;

(c) a base plate assembly adapted to, in the closed position, maintain an inner face of the top blade force plane substantially closely opposed to and just outside of, with respect to the central orifice axis during an orifice expansion, the outer face of the left blade force plane, while maintaining an inner face of the left blade force plane relatively close to the central orifice axis;

(d) the opposing blade means further adapted to remain fixed or move in a direction substantially opposite the lateral expansion direction of the top and left blades during such lateral expansion;

(e) a lateral motion forcing means is operatively attached to the base plate assembly such that activation of the lateral motion forcing means forces a rotating and sliding action in the base plate assembly which translates into forcing a lateral expansion of at least the left and top blades; and (f) the base plate assembly further adapted to, upon activation of the lateral motion forcing means from the closed position, expandingly move:
  (i) the left blade force plane laterally outward in a path substantially perpendicular to the left blade force plane and
  (ii) the top blade force plane simultaneously laterally outward and toward the top position together with and expandingly slightly ahead of the left blade force plane such that the two force planes form an effectively continuous and broader orifice expanding forcing plane than at the closed position.

2. The device of claim 1 wherein the opposing blade means comprise right and bottom blades whereby:

(g) the bottom and right blades lie within bottom and right blade force planes, respectively, and the outer faces of the bottom and right blades correspond to at least part of an outer face of the bottom and right blade force planes, respectively;

(h) the base plate assembly is further adapted to, in the closed position, maintain an inner face of the bottom blade force plane substantially closely opposed to and just outside of, with respect to the central orifice axis during an orifice expansion, the outer face of the right blade force plane, while maintaining an inner face of the right blade force plane relatively close to the central orifice axis;

(i) the lateral motion forcing means is further adapted such that activation of the lateral motion forcing means from the closed position forces a rotating and sliding action in the base plate means which translates into forcing at least a lateral expansion of the bottom and right blades; and (j) the base plate assembly further adapted to, upon activation of the lateral motion forcing means from the closed position, expandingly move:
  (i) the right blade force plane laterally outward in a path substantially perpendicular to the right blade force plane and
  (ii) the bottom blade force plane simultaneously laterally outward and toward a bottom position together with and expandingly slightly ahead of the right blade force plane such that the two force planes form an effectively continuous and broader orifice expanding forcing plane than at the closed position.

3. The device of claim 2 wherein the base plate assembly comprises two solid plates each with two ends and having operator and operant sides, whereby the lateral motion forcing means are substantially non-rotatingly fixed to the operator sides of the solid plates and to the operant side of separate solid plates are perpendicularly fixed the left and right blades.

4. The device of claim 3 wherein the base plate assembly further comprises two slotted plates, each with two ends and operator and operant sides, whereby each side is a surface of a plate parallel and spaced apart from the other, the spaced apart distance is about slightly greater than the thickness of a solid plate and adapted such that a non-pivoting pill end of a solid plate may be slidingly secured therein to effect the lateral and expansion motions of the blades, and one end of each slotted plate is attached by a pivoting pin connection to an end of a separate solid plate.

5. The device of claim 4 wherein the slotted plates comprise an inside edge with a notch out section adapted to provide space and means for manually and mechanically securing of out of a line of sight into an expanded orifice the extension shafts of instruments to be used for examination or manipulation of things within a cavity exposed by the expanded orifice.

6. The device of claim 4 wherein the top and bottom blades are perpendicularly secured to the operant sides of different slotted plates.

7. The device of claim 6 wherein the slotted plate securing the top blade is adapted at its non-pivoting pin end to release from effective sliding association the solid plate associated therewith and to be moved into a further expanded position to accommodate transfer of the extension shafts of instruments to be used for examination or manipulation of things within a cavity exposed by the expanded orifice from the an inside edge view to a notch out area in an outer edge of the just mentioned solid plate.

8. The device of claim 6 wherein the attachment of the top blade to the slotted plate is a hinge whereby the top blade is adapted to move its end distal to the hinge outward with respect to the central orifice axis while maintaining its other end in a fixed position.

9. The device of claim 6 wherein the blades comprise means for support for a removable blade and a removable blade.

10. The device of claim 1 wherein the base plate assembly comprises two solid plates each with two ends and having operator and operant sides, whereby the lateral motion forcing means are substantially non-rotatingly fixed to the operator sides of the solid plates and to the operant side of separate solid plates are perpendicularly fixed the left and right blades.

* * * * *